United States Patent
Tezuka et al.

(10) Patent No.: US 10,262,419 B2
(45) Date of Patent: Apr. 16, 2019

(54) ANALYSIS DEVICE AND ANALYSIS SYSTEM

(71) Applicant: KONICA MINOLTA, INC., Chiyoda-ku, Tokyo (JP)

(72) Inventors: Hidetake Tezuka, Tachikawa (JP); Tetsu Hosoki, Koganei (JP); Noritsugu Matsutani, Musashino (JP); Tomonori Gido, Kawasaki (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/611,746

(22) Filed: Jun. 1, 2017

(65) Prior Publication Data
US 2017/0352154 A1 Dec. 7, 2017

(30) Foreign Application Priority Data
Jun. 2, 2016 (JP) .................................. 2016-110541

(51) Int. Cl.
| | |
|---|---|
| G06T 7/00 | (2017.01) |
| A61B 5/11 | (2006.01) |
| A61B 5/113 | (2006.01) |
| A61B 6/00 | (2006.01) |
| H04N 5/232 | (2006.01) |
| H04N 5/268 | (2006.01) |
| H04N 5/775 | (2006.01) |
| H04N 5/77 | (2006.01) |

(52) U.S. Cl.
CPC ............ *G06T 7/0012* (2013.01); *A61B 5/113* (2013.01); *A61B 5/1128* (2013.01); *A61B 6/461* (2013.01); *A61B 6/50* (2013.01); *A61B 6/5217* (2013.01); *A61B 6/563* (2013.01); *H04N 5/23293* (2013.01); *H04N 5/268* (2013.01); *H04N 5/77* (2013.01); *H04N 5/775* (2013.01); *G06T 2207/10016* (2013.01); *G06T 2207/10116* (2013.01); *G06T 2207/20004* (2013.01); *G06T 2207/30048* (2013.01); *G06T 2207/30061* (2013.01)

(58) Field of Classification Search
CPC ......... G06T 7/0012; G06T 2207/20004; G06T 2207/10016; G06T 2207/30048; G06T 2207/30061; G06T 2207/10116; H04N 5/775; H04N 5/268; H04N 5/23293; A61B 6/50; A61B 5/1128; A61B 6/5217; A61B 6/461; A61B 5/113
USPC ....................................................... 382/128
See application file for complete search history.

(56) References Cited

U.S. PATENT DOCUMENTS 9,137,576 B2 * 9/2015 McRae ................. G06Q 30/06

FOREIGN PATENT DOCUMENTS

JP 2013039427 A 2/2013

* cited by examiner

*Primary Examiner* — Gregory F Cunningham
(74) *Attorney, Agent, or Firm* — Holtz, Holtz & Volek PC

(57) ABSTRACT

An analysis device includes a controller. The analysis device receives moving images sent from a plurality of imaging devices, analyzes the received moving images, and sends an analysis result of a moving image to, among a plurality of display devices, a display device which has made a request to display so that the display device displays the analysis result. The controller controls a processing order of reception processes and analysis processes on moving images sent from the imaging devices according to degrees of priority preset for the respective imaging devices.

17 Claims, 3 Drawing Sheets

ANALYSIS DEVICE AND ANALYSIS SYSTEM

CROSS-REFERENCE TO RELATED APPLICATIONS

The present U.S. patent application claims a priority under the Paris Convention of Japanese Patent Application No. 2016-110541 filed on Jun. 2, 2016, the entire disclosure of which, including the specification, claims, drawings and abstract, is incorporated herein by reference in its entirety.

BACKGROUND OF THE INVENTION

1. Field of the Invention

The present invention relates to an analysis device and an analysis system.

2. Description of the Related Art

There is known a dynamic analysis system which takes (captures) dynamic images of subjects with semiconductor image sensors, such as FPDs (Flat Panel Detector), and analyzes the obtained dynamic images and provides the same for diagnosis, instead of taking still images of subjects by radiation with conventional films/screens or photostimulable phosphor plates and providing the same for diagnosis. The dynamic analysis system is constituted of an imaging device which performs dynamic imaging with an FPD, a console which controls the imaging device and displays the taken image(s) to check, an analysis device which performs analysis based on the frame images obtained by dynamic imaging, and a display device which displays the analysis result. (Refer to, for example, Japanese Patent Application Publication No. 2013-039427.) In a hospital, imaging through diagnosis is performed in the following order: (1) a dynamic imaging step with an imaging device and a console; (2) an analysis step with an analysis device; and (3) a diagnosis step with a display device.

(1) Dynamic Imaging Step

In the dynamic imaging step, a radiologist positions a subject such that an examination target site is placed at a predetermined point of the imaging device in an imaging room, checks the posture of the subject, and performs exposure preparation. Next, the radiologist sets imaging conditions, presses an exposure switch (dynamic imaging), checks the obtained image(s), and so forth using the console in an operation room.

In the case of dynamic imaging of a chest part, according to the type of analysis or the like, the respiration state during imaging differs. For example, in the case of analysis of the ventilation function, imaging is performed in a quiet breathing state; in the case of analysis of the pulmonary perfusion function or analysis of the condition of the heart, imaging is performed in a breath holding state; and in the case of analysis of the maximum ventilation (breathing) capacity as one of the ventilation function, imaging is performed in a deep breathing state. Hence, for multiple types of analysis, imaging in multiple respiration states is necessary. Further, even for one type of analysis, imaging in multiple respiration states may be necessary, depending on the type of analysis. When one patient needs to be imaged in multiple respiration states, in general, the patient is instructed about a respiration state and imaged in the respiration state, and this is repeated for each respiration state. That is, for each respiration state, posture checking, exposure preparation, setting of the imaging conditions, dynamic imaging (exposure), image checking and so forth are repeated.

The frame images obtained by dynamic imaging are sent to the analysis device through the console.

(2) Analysis Step

In the analysis step, the analysis device first analyzes (analysis process) the dynamic image sent from the console with a default parameter set or a parameter set by an operator, such as a radiologist, and displays the analysis result on the display device in response to a request from the display device. An operator, such as a radiologist or a doctor, waits until the analysis process finishes, and checks the analysis result. If the obtained analysis result is not an appropriate analysis result to make a diagnosis, the operator adjusts the parameter set at least partly, and instructs the analysis device to perform the analysis process again. That is, until the appropriate analysis result is obtained, the operator repeatedly adjusts parameters, instructs the analysis device to reanalyze the dynamic image, waits until the (re)analysis result becomes available, and checks the (re)analysis result. Once the appropriate analysis result is obtained, the operator, such as a radiologist or a doctor, makes an instruction to store the analysis result in a storage unit, so that the analysis result is stored in the storage unit of the analysis device or the like.

(3) Diagnosis Step

In the diagnosis step, a doctor selects, from the taken dynamic images and their analysis results, a dynamic image and/or its analysis result of an examination based on which the doctor makes a diagnosis, displays the same on the display device, and makes a diagnosis.

By the way, if the dynamic imaging system has two or more imaging systems (devices), the analysis device receives and analyzes dynamic images sent from all of the imaging systems. Hence, if requests to send for dynamic images (i.e. requests to receive dynamic images) from the imaging systems come at once, the analysis process on a high urgency-required dynamic image may be put on the back burner. Further, the analysis device has a function as a server to offer the analysis results to display devices with which doctors make diagnoses. Hence, if requests from two or more display devices come at once, it may take long time until a doctor who needs to make a diagnosis urgently can see his/her requesting analysis result.

BRIEF SUMMARY OF THE INVENTION

Objects of the present invention include reducing waiting time for high urgency-required analysis results.

In order to achieve the above or other objects, according to a first aspect of the present invention, there is provided an analysis device including a controller, wherein the analysis device receives moving images sent from a plurality of imaging devices, analyzes the received moving images, and sends an analysis result of a moving image to, among a plurality of display devices, a display device which has made a request to display so that the display device displays the analysis result, and the controller controls a processing order of reception processes and analysis processes on moving images sent from the imaging devices according to degrees of priority preset for the respective imaging devices.

According to a second aspect of the present invention, there is provided an analysis system including: a plurality of imaging devices; a display device; and the analysis device.

According to a third aspect of the present invention, there is provided an analysis device including a controller, wherein the analysis device receives moving images sent from a plurality of imaging devices, analyzes the received moving images, and sends an analysis result of a moving image to, among a plurality of display devices, a display device which has made a request to display so that the display device displays the analysis result, and the controller controls a processing order of reception processes and analysis processes on moving images sent from the imaging devices according to degrees of priority preset for respective data attributes of the moving images.

According to a fourth aspect of the present invention, there is provided an analysis system including: a plurality of imaging devices; a display device; and the analysis device.

BRIEF DESCRIPTION OF THE SEVERAL VIEWS OF THE DRAWING

The present invention is fully understood from the detailed description given hereinafter and the accompanying drawings, which are given by way of illustration only and thus are not intended to limit the present invention, wherein.

DETAILED DESCRIPTION OF THE INVENTION

Hereinafter, embodiment(s) of the present invention is described in detail with reference to the drawings. However, the scope of the present invention is not limited to the embodiment or illustrated examples.

[Configuration of Dynamic Analysis System 100]

First, the configuration of a dynamic analysis system is described.

Figure 1:
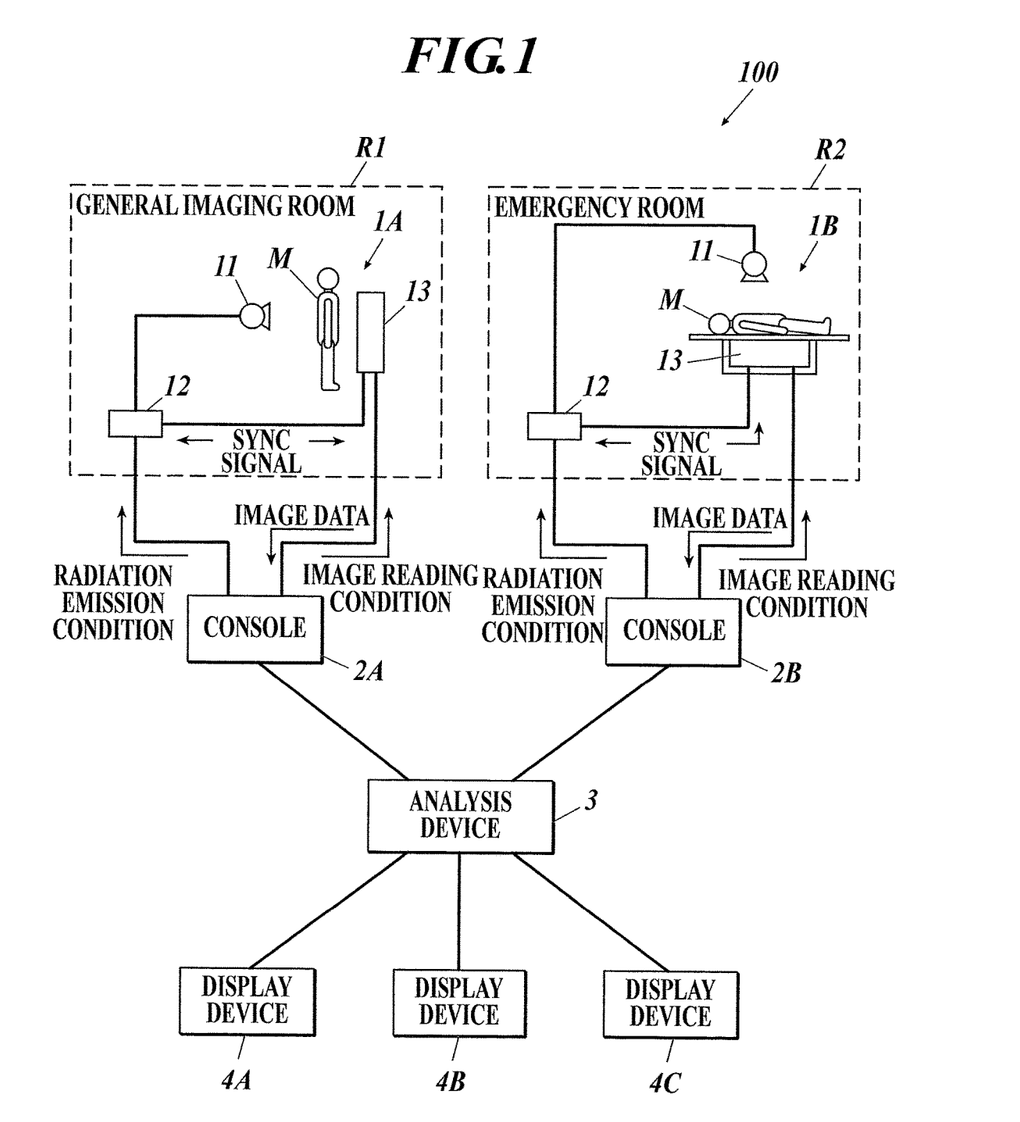
FIG. 1 shows an example of the overall configuration of a dynamic analysis system.

FIG. 1 shows an example of the overall configuration of a dynamic analysis system 100 according to an embodiment(s) of the present invention.

As shown in FIG. 1, the dynamic analysis system 100 includes: an imaging device 1A provided in a general imaging room R1; a console 2A which controls the imaging device 1A; an imaging device 1B provided in an emergency room R2; a console 2B which controls the imaging device 1B; an analysis device 3; and display devices 4A to 4C. The imaging device 1A and the console 2A are connected to one another via a communication cable or the like, and also the imaging device 1B and the console 2B are connected to one another via a communication cable or the like. The imaging device 1A and the console 2A work in cooperation with one another, and together constitute an imaging device of claims below. The same applies to the imaging device 1B and the console 2B. The analysis device 3 is connected with the console 2A, the console 2B, and each of the display devices 4A to 4C via communication networks, such as LAN (Local Area Network), so as to exchange data therebetween.

[Configurations of Imaging Devices 1A and 1B]

The imaging device 1A is an imager which images a cyclic dynamic state of a chest part, and includes a radiation source 11, a radiation emission control device 12 and a radiation detection unit 13. Examples of the cyclic dynamic state include: change in shape of the lungs, i.e. expansion and contraction of the lungs, accompanying respiration; and pulsation of the heart. Dynamic imaging is performed by repeatedly emitting pulsed radiation, such as X-rays, to a subject M at predetermined time intervals (pulse emission) or continuously emitting radiation without a break to a subject M at a low dose rate (continuous emission), thereby obtaining a plurality of images showing the dynamic state. A series of images obtained by dynamic imaging is called a dynamic image. Images constituting a dynamic image are called frame images. In the embodiment described hereinafter, as an example, dynamic imaging is performed by pulse emission.

The radiation source 11 is disposed to face the radiation detection unit 13 having a subject M in between, and emits radiation (X-rays) to the subject M under the control of the radiation emission control device 12.

The radiation emission control device 12 is connected to the console 2A, and controls the radiation source 11 based on radiation emission conditions input from the console 2A so as to perform radiation imaging. The radiation emission conditions input from the console 2A include a pulse rate, a pulse width, a pulse interval, the number of frames (frame images) to be taken by one imaging, a value of current of an X-ray tube, a value of voltage of the X-ray tube, and a type of added filter. The pulse rate is the number of times radiation is emitted per second, and matches the frame rate described below. The pulse width is a period of time for one radiation emission. The pulse interval is a period of time from the start of one radiation emission to the start of the next radiation emission, and matches the frame interval described below.

The radiation detection unit 13 is constituted of a semiconductor image sensor, such as an FPD, and disposed to face the radiation source 11 having a subject M in between. The radiation detection unit 13 (semiconductor image sensor, such as an FPD) is constituted of detection elements (pixels) arranged at predetermined points on a substrate, such as a glass substrate, in a matrix. The detection elements detect radiation (intensity of radiation) which has been emitted from the radiation source 11 and passed through at least the subject M, convert the detected radiation into electric signals, and accumulate the electric signals therein. The pixels are provided with switching elements, such as TFTs (Thin Film Transistors). The radiation detection unit 13 controls the switching elements of the pixels based on the image reading conditions input from the console 2A so as to switch the pixels to read the electric signals accumulated therein, thereby reading the electric signals accumulated in the pixels and obtaining image data. This image data is a frame image(s). The radiation detection unit 13 outputs the obtained frame images to the console 2A. The image reading conditions include a frame rate, a frame interval, a pixel size, and an image size (matrix size). The frame rate is the number of frame images to be obtained per second, and matches the pulse rate described above. The frame interval is a period of time from the start of one frame image obtaining action to the start of the next frame image obtaining action, and matches the pulse interval described above.

The radiation emission control device 12 and the radiation detection unit 13 are connected to one another, and exchange sync signals so as to synchronize the radiation emission actions with the image reading actions.

The imaging device 1B includes, as with the above-described imaging device 1A, a radiation source 11, a radiation emission control device 12 and a radiation detection unit 13. However, the radiation emission control device 12 and the radiation detection unit 13 of the imaging device 1B are connected to the console 2B. The radiation emission control device 12 controls the radiation source 11 based on the radiation emission conditions input from the console 2B so as to perform radiation imaging. The radiation detection unit 13 controls the switching elements of the pixels based on the image reading conditions input from the console 2B so as to read the electric signals accumulated in the pixels and obtain image data of frame images, and outputs the obtained image data of frame images to the console 2B.

[Configurations of Consoles 2A and 2B]

The console 2A is provided in an operation room near the general imaging room R1, and outputs the radiation emission conditions and the image reading conditions to the imaging device 1A so as to control the radiation imaging and the radiation image reading actions performed by the imaging device 1A, and also displays the dynamic image obtained by the imaging device 1A for a radiologist to check.

Figure 2:
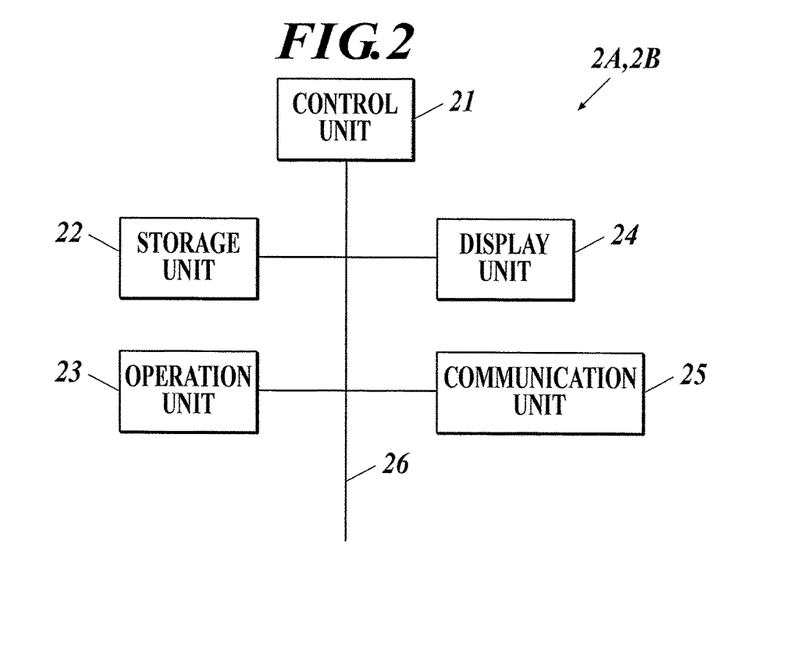
FIG. 2 is a block diagram showing the functional configuration of a console.

The console 2A includes, as shown in FIG. 2, a control unit 21, a storage unit 22, an operation unit 23, a display unit 24 and a communication unit 25. These units are connected to one another via a bus 26.

The control unit 21 includes a CPU (Central Processing Unit) and a RAM (Random Access Memory). The CPU of the control unit 21 reads a system program and various process programs stored in the storage unit 22 in response to operation on the operation unit 23, opens the read programs in the RAM, and, in accordance with the opened programs, performs concentrated control of actions of the units of the console 2A and the radiation emitting actions and the reading actions of the imaging device 1A.

The storage unit 22 is constituted of a nonvolatile semiconductor memory, a hard disk or the like. The storage unit 22 stores therein various programs to be executed by the control unit 21, parameters necessary to perform processes of the programs, data, such as process results, and so forth. The programs are stored in the form of a computer readable program code(s), and the control unit 21 acts in accordance with the program code.

The storage unit 22 also stores therein the radiation emission conditions and the image reading conditions for respective examination target sites (here, the chest part). The storage unit 22 also stores therein imaging order information sent from a not-shown RIS (Radiology Information System) or the like. The imaging order information contains patient information and examination information (examination ID, examination target site (here, the chest part), type of analysis (e.g. ventilation analysis, pulmonary perfusion analysis, measurement of the maximum ventilation capacity, etc.), data attribute (emergency, general outpatient, ward follow-up), etc.).

The operation unit 23 includes: a keyboard including cursor keys, number input keys and various function keys; and a pointing device, such as a mouse, and outputs, to the control unit 21, command (instruction) signals input by key operation on the keyboard or by mouse operation. The operation unit 23 may have a touch panel on a display screen of the display unit 24. In this case, the operation unit 23 outputs command signals input via the touch panel to the control unit 21.

The operation unit 23 also includes an exposure switch to instruct the radiation emission control device 12 to perform dynamic imaging.

The display unit 24 is constituted of a monitor, such as an LCD (Liquid Crystal Display) or a CRT (Cathode Ray Tube), and displays thereon input commands from the operation unit 23, data and so forth in accordance with commands of display signals input from the control unit 21.

The communication unit 25 includes a LAN adapter, a modem and a TA (Terminal Adapter), and controls data exchange with the analysis device 3 or the like connected to the communication network.

The console 2B is provided in an operation room near the emergency room R2. The console 2B includes, as with the console 2A, a control unit 21, a storage unit 22, an operation unit 23, a display unit 24 and a communication unit 25. These units are connected to one another via a bus 26. The console 2B performs concentrated control of actions of the units of the console 2B and the radiation emitting actions and the reading actions of the imaging device 1B.

[Configuration of Analysis Device 3]

The analysis device 3 receives the dynamic images sent from the consoles 2A and 23, analyzes the received dynamic images, and, in response to requests from the display devices 4A to 4C, sends the analysis results to the display devices 4A to 4C so that the display devices 4A to 4C display the analysis results or reanalyze the dynamic images. In the embodiment, the analysis device 3 performs dynamic analysis of chest parts based on the dynamic images sent from the consoles 2A and 2B.

Figure 3:
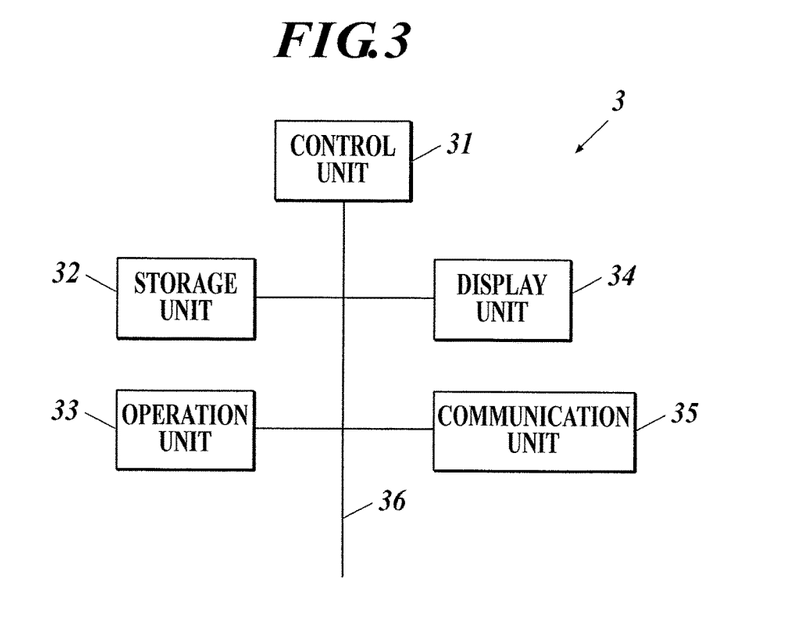
FIG. 3 is a block diagram showing the functional configuration of an analysis device.

The analysis device 3 includes, as shown in FIG. 3, a control unit 31 (controller), a storage unit 32, an operation unit 33, a display unit 34 and a communication unit 35. These units are connected to one another via a bus 36.

The control unit 31 includes a CPU and a RAM. The CPU of the control unit 31 reads a system program and various process programs stored in the storage unit 32 in response to operation on the operation unit 33, opens the read programs in the RAM, and, in accordance with the opened programs, performs concentrated control of actions of the units of the analysis device 3. Further, the control unit 31 performs reception processes and analysis processes on dynamic images in cooperation with the program(s) stored in the storage unit 32. Still further, the control unit 31 causes the display unit 34 to display the analysis results or sends the analysis results to the display devices 4A to 4C so that the display devices 4A to 4C display the analysis results, in response to requests from the operation unit 33 or the display devices 4A to 4C.

The storage unit 32 is constituted of a nonvolatile semiconductor memory, a hard disk or the like. The storage unit 32 stores therein various programs, parameters necessary to perform processes of the programs, data, such as process results, and so forth. The programs are stored in the form of a computer readable program code(s), and the control unit 31 acts in accordance with the program code.

The storage unit 32 also stores therein list information which contains the patient information, the examination information and status information (progress status, such as "receiving", "analyzing" and "analyzed") on each dynamic image which the analysis device 3 has started to receive from the console 2A or 2B. The storage unit 32 also stores therein the analysis results associated with the respective dynamic images.

The operation unit 33 includes: a keyboard including cursor keys, number input keys and various function keys; and a pointing device, such as a mouse, and outputs, to the control unit 31, command (instruction) signals input by key operation on the keyboard or by mouse operation. The operation unit 33 may have a touch panel on a display screen of the display unit 34. In this case, the operation unit 33 outputs command signals input via the touch panel to the control unit 31.

The display unit 34 is constituted of a monitor, such as an LCD or a CRT, and performs various types of display in accordance with commands of display signals input from the control unit 31.

The communication unit 35 includes a LAN adapter, a modem and a TA, and controls data exchange with the devices connected to the communication networks.

[Configurations of Display Devices 4A to 4C]

Figure 4:
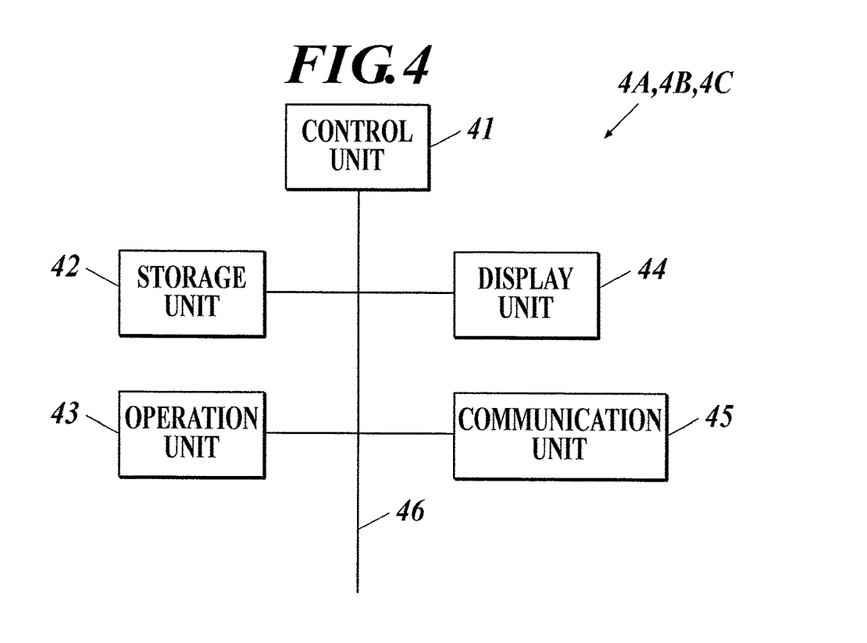
FIG. 4 is a block diagram showing the functional configuration of a display device.

As shown in FIG. 4, each of the display devices 4A to 4C includes a control unit 41, a storage unit 42, an operation unit 43, a display unit 44 and a communication unit 45. These units are connected to one another via a bus 46. Each of the display devices 4A to 4C is provided in a consultation room or the like, and obtains a dynamic image and its analysis result from the analysis device 3 in response to an operation by a radiologist, a doctor or the like, and displays the same on a viewer screen described below. Further, each of the display devices 4A to 4C displays a process specifying screen, described below, in response to a command (instruction) from the operation unit 43, there accepts adjustment of parameters in response to input from the operation unit 43, and instructs the analysis device 3 to reanalyze a dynamic image with the adjusted parameters.

[Flow of Actions of Dynamic Analysis System 100]

Figure 5:
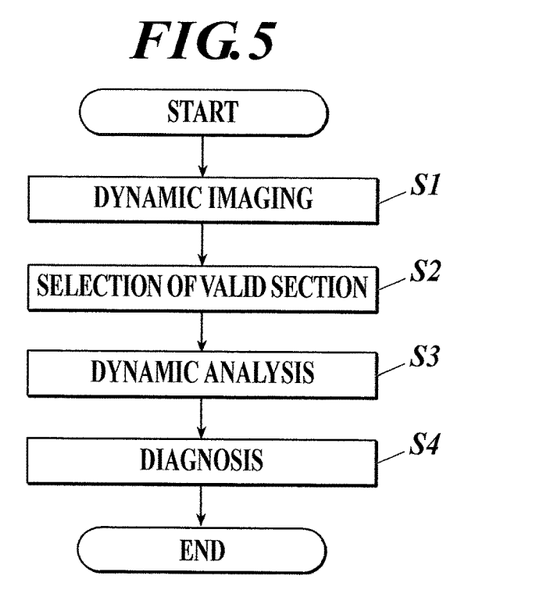
FIG. 5 is a flowchart showing flow of actions in the dynamic analysis system.

Next, flow of actions in the dynamic analysis system 100 is described. FIG. 5 is a flowchart showing the flow of actions in the dynamic analysis system 100.

First, dynamic imaging is performed by the imaging device 1A in the general imaging room R1 and the console 2A or by the imaging device 1B in the emergency room R2 and the console 2B (Step S1).

For example, if a subject M is an emergency patient, dynamic imaging is performed by the imaging device 1B in the emergency room R2 and the console 2B, whereas if the subject M is not an emergency patient, dynamic imaging is performed by the imaging device 1A in the general imaging room R1 and the console 2A.

More specifically, a radiologist selects, using the operation unit 23, imaging order information on the next examination from a list screen where a list of imaging order information is displayed, the list screen being displayed on the display unit 24 of the console 2A or 2B, and checks the examination target site (here, the chest part) and the type of analysis (e.g. ventilation analysis, pulmonary perfusion analysis, measurement of the maximum ventilation capacity, etc.). Next, the radiologist positions the patient (subject M) such that the examination target site is placed at a predetermined point of the imaging device 1A or 2A, checks the posture of the patient, and performs exposure preparation. Next, the radiologist sets the imaging conditions and presses the exposure switch (dynamic imaging) using the operation unit 23 of the console 2A or 2B, and checks the dynamic image obtained by dynamic imaging of the imaging device 1A or 1B and displayed on the display unit 24.

Note that, when one patient needs to be imaged in multiple respiration states, for example, for multiple types of analysis (e.g. ventilation analysis, pulmonary perfusion analysis, measurement of the maximum ventilation capacity, etc.), conventionally, imaging of the patient is performed for each respiration state. That is, for each respiration state, patient posture checking, exposure preparation, setting of the imaging conditions, dynamic imaging (exposure), image checking and so forth are repeated. Hence, it takes long time to finish all the imaging (multiple times of dynamic imaging) of one patient.

In the embodiment, when one patient needs to be imaged in multiple respiration states, the patient is imaged in these different respiration states by one dynamic imaging. That is, after patient posture checking, exposure preparation, and setting of the imaging conditions, the radiologist instructs the patient about the first respiration, state and presses the exposure switch of the console 2A or 2B. In response to the press on the exposure switch, the control unit 21 controls the imaging device 1A or 1B to start imaging. After a predetermined time elapses from the start of imaging, the radiologist instructs the patient about another respiration state. When imaging in all the necessary respiration states finishes, the radiologist releases the exposure switch to stop imaging, and checks the dynamic image. When an instruction "Imaging OK" is input through the operation unit 23, the control unit 21 attaches, to the obtained frame images, information such as an ID to identify the dynamic image, the patient information, the examination information, the radiation emission conditions, the image reading conditions, the respective numbers indicating what number in the imaging order the respective frame images have been taken (frame numbers) and identification information on the console, and sends the same to the analysis device 3 through the communication unit 25 of the console 2A or 2B. Thus, in the embodiment, even when a patient needs to be imaged in multiple respiration states, posture checking, exposure preparation, setting of the imaging conditions, press on the exposure switch and image checking need to be performed only one time. This can greatly reduce time required for dynamic imaging.

In the analysis device 3, when receiving a request to send for a dynamic image from the console 2A or 2B through the communication unit 35, the control unit 31 starts the reception process, add, to the list information stored in the storage unit 32, the patient information, the examination information and so forth on the dynamic image which the control unit 31 has started to receive (reception process), and sets the status of the dynamic image to "receiving". When finishing receiving the series of frame images of the dynamic image, the control unit 31 changes the status of the dynamic image in the list information to "analyzing", and analyzes the dynamic image to select, from the series of frame images, a valid section constituted of valid frame images for analysis in Step S3 described below (Step S2).

For example, in the case of ventilation analysis, a section of quiet breathing as the respiration state, in the case of pulmonary perfusion analysis, a section of breath holding as the respiration state, and in the case of the maximum ventilation capacity, a section of deep breathing as the respiration state are selected as the valid section for analysis.

Note that, instead of the analysis device 3, the console 2A or 2B may select the valid section, and send only the frame images of the valid section to the analysis device 3.

After selecting the valid section, the control unit 31 of the analysis device 3 analyzes the selected valid section (frame images) of the dynamic image (analysis process) (Step S3).

In Step S3, the control unit 31 performs the analysis process according to the type of analysis attached to the dynamic image. At the time, the control unit 31 performs the analysis process with a predetermined parameter set automatically, or performs the analysis process with a parameter set by an operator operating the operation unit 33. As the analysis process, publically-known analysis processes, such as ventilation analysis and pulmonary perfusion analysis described, for example, in Japanese Patent Application Publication No. 2012-110451, are applicable.

When finishing the analysis process, the control unit 31 changes the status of the dynamic image in the list information stored in the storage unit 32 to "analyzed", and associates and stores the analysis result with the ID of the dynamic image, the frame numbers, the parameter set used for the analysis process and so forth in the storage unit 32. Note that the control unit 31 may, additionally, automatically set a parameter set which is the same type as but has different values from the parameter set used for the first analysis process, perform the (second) analysis process with this parameter set, and associate and store the analysis result with the ID of the dynamic image, the frame numbers, the parameter set used for the (second) analysis process and so forth in the storage unit 32.

Here, if an operator (user), such as a radiologist or a doctor, logs on to one of the display devices 4A to 4C and accesses the analysis device 3, the control unit 41 of the display device 4A, 4B or 4C to which the operator logs on obtains the list information from the analysis device 3 through the communication unit 45, and causes the display unit 44 to display the list screen (list information). When the operator selects, using the operation unit 43, an examination from the list information displayed on the display unit 44, the control unit 41 causes the display unit 44 to display the viewer screen regarding the selected examination, and requests the analysis device 3 to send the analysis result of the dynamic image of the selected examination for display (i.e. makes a request to display). The viewer screen is a screen where a dynamic image(s) and its analysis result(s) are displayed. If the operator selects an examination having the status "analyzed" using the operation unit 43, the analysis result is sent from the analysis device 3 and displayed on the viewer screen. From the viewer screen, the process specifying screen to set/adjust a/the parameter set for the analysis process can be opened. When the operator sees the analysis result, and if finds that the analysis result is not an appropriate analysis result to make a diagnosis, the operator operates the operation unit 43 to open the process specifying screen from the viewer screen, and there adjusts the parameter set. Then, the control unit 41 requests the analysis device 3 to reanalyze the dynamic image with the adjusted parameter set (reanalysis process) and send the reanalysis result for display, obtains the reanalysis result from the analysis device 3, and causes the display unit 44 to display the reanalysis result on the viewer screen.

After the analysis process, a doctor makes a diagnosis using the display device 4A, 4B or 4C (Step S4).

As described above, the doctor selects an examination from the list screen of the display device 4A, 4B or 4C to display the dynamic image and/or the analysis result of the examination, and studies the same. An emergency physician or the like can study a dynamic image(s) taken by the imaging device 1B in the emergency room R2 and its analysis result(s) before a non-emergency physician or the like who studies a dynamic image(s) taken by the imaging device 1A in the general imaging room R1 and its analysis result(s). The doctor makes a diagnosis based on the result of study.

As shown in FIG. 1, in the dynamic analysis system 100, the analysis device 3 is connected with a plurality of consoles (i.e. the consoles 2A and 2B) and a plurality of display devices (i.e. the display devices 4A to 4C). Hence, as described in the "Control Example 1" and "Control Example 2" below, in order to allow a doctor who makes a diagnosis based on an analysis result of a dynamic image of a patient who is in urgent need of care to see the analysis result with a shorter waiting time, the control unit 31 of the analysis device 3 controls the processing order of the reception processes and the analysis processes on dynamic images and processes requested by the display devices 4A to 4C. In the "Control Example 1" and "Control Example 2", the reception process and the analysis process on a dynamic image are sequentially performed (e.g. after the reception process on a dynamic image A, the analysis process on the dynamic image A is performed, and after the analysis process on the dynamic image A, the reception process and the analysis process on a dynamic image B are performed). However, this is not a limitation.

Note that the storage unit 32 stores (sets) therein degrees of priority for respective consoles connected to the analysis device 3, degrees of priority for respective data attributes of dynamic images, and degrees of priority for respective users (operators, e.g. radiologists and doctors (clinicians, emergency physicians, etc.)) of display devices connected to the analysis device 3. The storage unit 32 also stores therein points for the degrees of priority by being associated with the degrees of priority (e.g. the degree of priority of 1 (first priority)=10 points, the degree of priority of 2 (second priority)=5 points, and the degree of priority of 3 (third priority)=2 points). In the embodiment, for example, degrees of priority for consoles are "console 2B>console 2A", and degrees of priority for data attributes are "emergency>general outpatient>ward follow-up".

Control Example 1

First, the control example 1 is described.

When receiving a request to send for a dynamic image from the console 2A or 2B, the control unit 31 performs the reception process on the dynamic image to receive the dynamic image through the communication unit 35. Next, the control unit 31 performs the analysis process thereon based on the type of analysis attached to the received dynamic image.

If receiving requests to send for dynamic images from the consoles 2A and 2B at the same time, the control unit 31 compares the degrees of priority preset for the respective consoles, and performs the reception processes with the communication unit 35 and the analysis processes on the dynamic images in order of priority (i.e. in descending order of priority). If the degrees of priority for the consoles 2A and 2B are the same, the control unit 31 compares the degrees of priority preset for the respective data attributes of the dynamic images which the consoles are going to send, and performs the reception processes with the communication unit 35 and the analysis processes on the dynamic images in order of priority.

If, during the reception process on a dynamic image, receiving another request(s) to send for a dynamic image(s) from the console 2A and/or the console 2B, the control unit 31 compares the degrees of priority preset for the console having sent the dynamic image being currently processed (currently-in-process dynamic image) and the console having sent the other request to send (if they are the same, compares the degrees of priority preset for the data attribute of the currently-in-process dynamic image and the data attribute of the dynamic image of the other request to send). If, as a result of the comparison, the degree of priority for the console having sent the currently-in-process dynamic image (the degree of priority for the data attribute of the currently-in-process dynamic image if the degrees of priority for the consoles are the same) is higher, the control unit 31 first completes the reception process and the analysis process (i.e. the sequence of processes) on the currently-in-process dynamic image, and then performs the reception process and the analysis process on the dynamic image of the other request to send. On the other hand, if the degree of priority for the console having sent the currently-in-process dynamic image (the degree of priority for the data attribute of the currently-in-process dynamic image if the degrees of priority for the consoles are the same) is lower, the control unit 31 first completes the reception process on the currently-in-process dynamic image, suspends the sequence of processes on the currently-in-process dynamic image, performs and completes the reception process and the analysis process on the dynamic image of the other request to send, and then restarts the suspended sequence of processes. Alternatively, it is possible that the control unit 31 suspends the reception process on the currently-in-process dynamic image without completing it, performs and completes the reception process and the analysis process on the dynamic image of the other request to send, and then restarts the suspended reception process.

If, during the analysis process on a dynamic image, receiving another request(s) to send for a dynamic image(s) from the console 2A and/or the console 2B, the control unit 31 first completes the analysis process on the currently-in-process dynamic image, and then performs the reception process and the analysis process on the dynamic image of the other request to send. Alternatively, it is possible that the control unit 31 compares the degrees of priority preset for the console having sent the currently-in-process dynamic image and the console having sent the other request to send (if they are the same, compares the degrees of priority preset for the data attribute of the currently-in-process dynamic image and the data attribute of the dynamic image of the other request to send). If, as a result of the comparison, the degree of priority for the console having sent the currently-in-process dynamic image (the degree of priority for the data attribute of the currently-in-process dynamic image if the degrees of priority for the consoles are the same) is lower, the control unit 31 suspends the analysis process on the currently-in-process dynamic image without completing it, performs and completes the reception process and the analysis process on the dynamic image of the other request to send, and then restarts the suspended analysis process.

Thus, the analysis device 3 performs control to perform the reception processes and the analysis processes on dynamic images in the descending order of the degrees of priority preset for the consoles which are going to/have sent the dynamic images. Further, if receiving requests to send for dynamic images at the same time from the consoles having the same degree of priority, the analysis device 3 performs control to perform the reception processes and the analysis processes on the dynamic images in the descending order of the degrees of priority preset for the data attributes of the dynamic images which the consoles are going to send. Therefore, for example, in the case where dynamic images handled by consoles are different from each other in urgency as described in the embodiment, a high urgency-required dynamic image can be received and analyzed prior to the other(s), and accordingly time required to make a high urgency-required analysis result displayable (i.e. available) can be reduced.

If requested to perform processes (i.e. receiving process requests which include: a request to display for an analysis result; and a request for a reanalysis process with an adjusted parameter set and for its analysis result for display) from two or more display devices among the analysis device 3 and the display devices 4A to 4C (here, the display unit 34 of the analysis device 3 is also a display device) at the same time, the control unit 31 compares the degrees of priority preset for the respective operators (users who log on) of the display devices which have made the requests, and performs the requested processes in order, starting from the process requested by a display device operated by a user for whom the highest degree of priority is preset. Examples of the processes include: sending an analysis result to a display device for display in response to a request to display (i.e. performing a display allowing process); and performing a reanalysis process based on an instruction by an operator of a display device and sending the analysis result to the display device for display. The analysis device 3 may leave a request(s) from the other display device(s) waiting until completing a process requested by one display device or may perform a process requested by another display device within a gap time (e.g. within a predetermined waiting time for an instruction on a reanalysis process after sending an analysis result). Further, the control unit 31 puts restrictions on access to a dynamic image in reception process or analysis process (currently-in-process dynamic image). That is, if instructed to perform the display allowing process of an analysis result or the reanalysis process on the currently-in-process dynamic image through a display device, the control unit 31 sends, without performing the requested process, the status information, such as "in process" ("receiving" or "analyzing" to be specific), to the display device so that the display device displays the status information.

If, during the reception process or the analysis process on a dynamic image, receiving a process request for another dynamic image from a display device, the control unit 31 compares, for example, (i) an added value (sum) of (a) points for the degree of priority preset for the console which has sent the currently-in-process dynamic image and (b) points for the degree of priority preset for the data attribute of the currently-in-process dynamic image with (ii) an added value (sum) of (a) points for the degree of priority preset for the console which had sent the other dynamic image of the process request (process-requested dynamic image), (b) points for the degree of priority preset for the data attribute of the process-requested dynamic image and (c) points for the degree of priority for the operator of the display device which has sent the process request. If, as a result of the comparison, the value of the former is higher, the control unit 31 first completes the reception process and the analysis process on the currently-in-process dynamic image, and then performs the process requested by the display device. On the other hand, if the value of the latter is higher, the control unit 31 suspends the current process (i.e. the reception process or the analysis process on the currently-in-process dynamic image), performs and completes the process requested by the display device, and then restarts the suspended process.

Thus, if receiving requests to display or the like from two or more display devices at the same time, the analysis device 3 performs the requested processes according to the degrees of priority preset for the respective operators of the display devices which have sent the requests to display or the like. Hence, waiting time for an analysis result can be reduced for a doctor who makes a diagnosis based on a high urgency-required examination. Further, if instructed to perform the display allowing process of an analysis result or the reanalysis process on the dynamic image in reception process or analysis process through a display device, the analysis device 3 sends, without performing the requested process, the status information, such as "in process", to the display device so that the display device displays the status information. Hence, the operator of the display device can understand that analysis thereof has not finished yet. Further, the analysis device 3 puts restrictions on access to the dynamic image in reception process or analysis process. Hence, suspension of the process can be prevented.

The operators of the analysis device 3 and the display devices 4A to 4C can each make an instruction to let a process be performed not in the order of the preset degrees of priority. The above-described list screen is provided with urgent buttons or the like for the respective examinations, and when an urgent button is pressed with the operation unit 33 (the operation unit 43) (i.e. the control unit 31 is instructed to perform a process on a dynamic image of an examination urgently), the control unit 31 ignores the preset degrees of priority for the dynamic image of the examination for which the urgent button has been pressed, gives the top priority to the dynamic image, and performs the instructed process, such as the display allowing process of the analysis result or the reanalysis process on the dynamic image. This makes it possible to flexibly deal with, for example, the case where an operator whose priority is low needs an analysis result urgently.

Control Example 2

First, the control example 2 is described.

When receiving a request to send for a dynamic image from the console 2A or 2B, the control unit 31 performs the reception process on the dynamic image to receive the dynamic image through the communication unit 35. Next, the control unit 31 performs the analysis process thereon based on the type of analysis attached to the received dynamic image.

If receiving requests to send for dynamic images from the consoles 2A and 2B at the same time, the control unit 31 compares the degrees of priority preset for the respective data attributes of the dynamic images which the consoles are going to send, and performs the reception processes with the communication unit 35 and the analysis processes on the dynamic images in order of priority (i.e. in descending order of priority). If the degrees of priority for the data attributes of the dynamic images which the consoles are going to send are the same, the control unit 31 compares the degrees of priority preset for the respective consoles, and performs the reception processes with the communication unit 35 and the analysis processes on the dynamic images in order of priority.

If, during the reception process on a dynamic image, receiving another request(s) to send for a dynamic image(s) from the console 2A and/or the console 2B, the control unit 31 compares the degrees of priority preset for the data attribute of the dynamic image being currently processed (currently-in-process dynamic image) and the data attribute of the dynamic image of the other request to send (if they are the same, compares the degrees of priority preset for the console having sent the currently-in-process dynamic image and the console having sent the other request to send). If, as a result of the comparison, the degree of priority for the data attribute of the currently-in-process dynamic image (the degree of priority for the console having sent the currently-in-process dynamic image if the degrees of priority for the data attributes of the dynamic images are the same) is higher, the control unit 31 first completes the reception process and the analysis process (i.e. the sequence of processes) on the currently-in-process dynamic image, and then performs the reception process and the analysis process on the dynamic image of the other request to send. On the other hand, if the degree of priority for the data attribute of the currently-in-process dynamic image (the degree of priority for the console having sent the currently-in-process dynamic image if the degrees of priority for the data attributes of the dynamic images are the same) is lower, the control unit 31 first completes the reception process on the currently-in-process dynamic image, suspends the sequence of processes on the currently-in-process dynamic image, performs and completes the reception process and the analysis process on the dynamic image of the other request to send, and then restarts the suspended sequence of processes. Alternatively, it is possible that the control unit 31 suspends the reception process on the currently-in-process dynamic image without completing it, performs and completes the reception process and the analysis process on the dynamic image of the other request to send, and then restarts the suspended reception process.

If, during the analysis process on a dynamic image, receiving another request(s) to send for a dynamic image(s) from the console 2A and/or the console 2B, the control unit 31 first completes the analysis process on the currently-in-process dynamic image, and then performs the reception process and the analysis process on the dynamic image of the other request to send. Alternatively, it is possible that the control unit 31 compares the degrees of priority preset for the data attribute of the currently-in-process dynamic image and the data attribute of the dynamic image of the other request to send (if they are the same, compares the degrees of priority preset for the console having sent the currently-in-process dynamic image and the console having sent the other request to send). If, as a result of the comparison, the degree of priority for the data attribute of the currently-in-process dynamic image (the degree of priority for the console having sent the currently-in-process dynamic image if the degrees of priority for the data attributes of the dynamic images are the same) is lower, the control unit 31 suspends the analysis process on the currently-in-process dynamic image without completing it, performs and completes the reception process and the analysis process on the dynamic image of the other request to send, and then restarts the suspended analysis process.

Thus, the analysis device 3 performs control to perform the reception processes and the analysis processes on dynamic images in the descending order of the degrees of priority preset for the data attributes of the dynamic images which the consoles are going to send/have sent. Further, if receiving requests to send for dynamic images, the data attributes of which have the same degree of priority, at the same time, the analysis device 3 performs control to perform the reception processes and the analysis processes on the dynamic images in the descending order of the degrees of priority preset for the consoles which are going to send the dynamic images. Therefore, for example, in the case where dynamic images handled by consoles are different from each other in urgency as described in the embodiment, a high urgency-required dynamic image can be received and analyzed prior to the other(s), and accordingly time required to make a high urgency-required analysis result displayable (i.e. available) can be reduced.

The actions of the control unit 31 when receiving requests to display for dynamic images, when receiving a request to display for a dynamic image during the reception process or the analysis process on another dynamic image, and when an urgent button is pressed and also the effects are the same as those described in the "Control Example 1", and therefore the descriptions thereof are not repeated here.

Although embodiment(s) of the present invention is described above, those described in the above embodiment are preferred examples of the present invention, and not intended to limit the present invention.

For example, in the above embodiment, dynamic images are received, analyzed and displayed or sent to be displayed by the analysis device 3. However, the present invention is also applicable to the case where not dynamic images but other types of moving images are received, analyzed and displayed or sent to be displayed.

Further, in the above embodiment, points are used to determine the processing order of processes in the case where the analysis device 3 receives a process request from the display device 4A, 4B or 4C during the reception process or the analysis process on a dynamic image. However, points may be used to determine the processing order of the reception processes and the analysis processes on dynamic images. For example, if points for the degree of priority for the console which is going to send/has sent a first dynamic image are 5 points and points for the degree of priority for the data attribute of the dynamic image are 5 points, whereas points for the degree of priority for the console which is going to send/has sent a second dynamic image are 2 points and points for the degree of priority for the data attribute of the dynamic image are 10 points, the reception process and the analysis process on the second dynamic image are given priority (performed first).

Further, in the above embodiment, the degrees of priority for the consoles are prior to the degrees of priority for the data attributes in the "Control Example 1", and the degrees of priority for the data attributes are prior to the degrees of priority for the consoles in the "Control Example 2". However, which comes first, the degree of priority for the consoles or the degrees of priority for the data attributes, may not be determined. Instead of that, weight allocation (weighting), such as "points for the degree of priority for an imaging device (console)×0.4" and "points for the degree of priority for an data attribute×0.6", may be used to determine which process is given priority. The degrees of priority for the consoles, the degrees of priority for the data attributes and the like and the ratio of weights in the weight allocation can be changed flexibly according to the operation of each facility.

Further, in the above embodiment, one imaging device is connected to one console. However, a plurality of imaging devices may be connected to one console. In this case, each imaging device connected to the console constitutes an imaging device of claims below. Then, for example, the storage unit 32 of the analysis device 3 stores therein degrees of priority for the respective imaging devices, and the control unit 31 of the analysis device 3 controls the processing order by using the degrees of priority for the imaging devices instead of the degrees of priority for the consoles.

In addition to the above, detailed configurations and detailed actions of the devices or the like of the dynamic analysis system 100 can also be appropriately modified without departing from the spirit of the present invention.

What is claimed is:

1. An analysis device comprising a controller, wherein:
   the analysis device receives moving images sent from a plurality radiation imaging devices, analyzes the received moving images, and sends an analysis result of a moving image to, among a plurality of display devices, a display device which has made a request to display so that the display device displays the analysis result, and
   the controller controls a processing order of reception processes and analysis processes on moving images sent from the radiation imaging devices according to degrees of priority preset for the respective radiation imaging devices.

2. The analysis device according to claim 1, wherein the controller controls the processing order of the reception processes and the analysis processes on the moving images sent from the radiation imaging devices according to degrees of priority preset for respective data attributes of the moving images in addition to the degrees of priority preset for the respective radiation imaging devices.

3. An analysis device comprising a controller, wherein:
   the analysis device receives moving images sent from a plurality of radiation imaging devices, analyzes the received moving images, and sends an analysis result of a moving image to, among a plurality of display devices, a display device which has made a request to display so that the display device displays the analysis result, and
   the controller controls a processing order of reception processes and analysis processes on moving images sent from the radiation imaging devices according to degrees of priority preset for respective data attributes of the moving images.

4. The analysis device according to claim 3, wherein the controller controls the processing order of the reception processes and the analysis processes on the moving images sent from the radiation imaging devices according to degrees of priority preset for the respective radiation imaging devices in addition to the degrees of priority preset for the respective data attributes of the moving images.

5. The analysis device according to claim 1, wherein the controller controls a processing order of processes requested by the display devices according to degrees of priority preset for respective users of the display devices.

6. The analysis device according to claim 3, wherein the controller controls a processing order of processes requested by the display devices according to degrees of priority preset for respective users of the display devices.

7. The analysis device according to claim 1, wherein the controller sends status information on a moving image which is in a reception process or an analysis process to the display device so that the display device displays the status information.

8. The analysis device according to claim 3, wherein the controller sends status information on a moving image which is in a reception process or an analysis process to the display device so that the display device displays the status information.

9. The analysis device according to claim 1, wherein the controller gives top priority to a process on a moving image which the controller has been instructed to process urgently through the display device.

10. The analysis device according to claim 3, wherein the controller gives top priority to a process on a moving image which the controller has been instructed to process urgently through the display device.

11. The analysis device according to claim 1, wherein the controller puts a restriction on access to a moving image which is in a reception process or an analysis process.

12. The analysis device according to claim 3, wherein the controller puts a restriction on access to a moving image which is in a reception process or an analysis process.

13. An analysis system comprising:
    a plurality of radiation imaging devices;
    a display device; and
    the analysis device according to claim 1.

14. An analysis system comprising:
    a plurality of radiation imaging devices;
    a display device; and
    the analysis device according to claim 3.

15. An analysis device comprising a controller, wherein:
the analysis device receives moving images sent from a plurality of radiation imaging devices, analyzes the received moving images, and sends an analysis result of a moving image to, among a plurality of display devices, a display device which has made a request to display so that the display device displays the analysis result,
the controller controls a processing order of reception processes and analysis processes on moving images sent from the radiation imaging devices according to at least one of (i) degrees of priority preset for the respective radiation imaging devices and (ii) degrees of priority preset for respective data attributes of the moving images, and
the moving images sent from the radiation imaging devices are chest moving images.

16. The analysis device according to claim 15, wherein the analysis processes are ventilation analysis processes or pulmonary perfusion analysis processes.

17. The analysis device according to claim 15, wherein the analysis processes are performed based on types of analysis attached to the respective moving images.

* * * * *